(12) United States Patent
Shibuya

(10) Patent No.: US 11,032,909 B2
(45) Date of Patent: Jun. 8, 2021

(54) ELECTRONIC APPARATUS

(71) Applicant: Renesas Electronics Corporation, Tokyo (JP)

(72) Inventor: Hiroki Shibuya, Tokyo (JP)

(73) Assignee: Renesas Electronics Corporation, Tokyo (JP)

( * ) Notice: Subject to any disclaimer, the term of this patent is extended or adjusted under 35 U.S.C. 154(b) by 637 days.

(21) Appl. No.: 15/296,114

(22) Filed: Oct. 18, 2016

(65) Prior Publication Data

US 2017/0164476 A1 Jun. 8, 2017

(30) Foreign Application Priority Data

Dec. 8, 2015 (JP) .............................. JP2015-239628

(51) Int. Cl.
| | |
|---|---|
| *H05K 1/18* | (2006.01) |
| *A61B 5/00* | (2006.01) |
| *A61B 5/0205* | (2006.01) |
| *G01J 1/44* | (2006.01) |
| *A61B 5/024* | (2006.01) |

(52) U.S. Cl.
CPC ............. *H05K 1/18* (2013.01); *A61B 5/0008* (2013.01); *A61B 5/02055* (2013.01); *A61B 5/681* (2013.01); *G01J 1/44* (2013.01); *A61B 5/02427* (2013.01); *A61B 2562/0219* (2013.01); *A61B 2562/0223* (2013.01); *A61B 2562/0233* (2013.01); *A61B 2562/0238* (2013.01); *A61B 2562/0247* (2013.01); *A61B 2562/12* (2013.01); *G01J 2001/446* (2013.01)

(58) Field of Classification Search
CPC ... A61B 5/02416; A61B 5/02438; A61B 8/02; A61B 5/6803; H05K 1/144; H05K 1/14
See application file for complete search history.

(56) References Cited

U.S. PATENT DOCUMENTS

| | | | |
|---|---|---|---|
| 2004/0236233 A1* | 11/2004 | Kosuda | .............. A61B 5/02416 600/485 |
| 2006/0229520 A1 | 10/2006 | Yamashita et al. | |
| 2009/0201656 A1* | 8/2009 | Shibuya | .............. H01L 25/0657 361/782 |

(Continued)

FOREIGN PATENT DOCUMENTS

| | | |
|---|---|---|
| JP | 2001-245860 A | 9/2001 |
| JP | 2006-312010 A | 11/2006 |

*Primary Examiner* — Christian Jang
*Assistant Examiner* — Karen E Toth
(74) *Attorney, Agent, or Firm* — SGPatents PLLC

(57) ABSTRACT

The invention aims at downsizing a sensor node incorporating a biosensor to detect biological information and at improving the accuracy of detection made by the biosensor and ensures a quality of communication performed by the sensor node. In the sensor node, a sensor section with a pulse wave sensor formed therein and a main body section with a data processing unit and a wireless communication unit formed therein are separated. The sensor section includes an A/D converter unit that converts an analog signal corresponding to biological information detected by the pulse wave sensor to a digital signal. Digital signal transmission is performed from the A/D converter unit to the data processing unit. Moreover, in the sensor node, there is no conductive member that planarly overlaps with an antenna.

9 Claims, 12 Drawing Sheets

(56) References Cited

U.S. PATENT DOCUMENTS

| | | | |
|---|---|---|---|
| 2015/0057511 A1* | 2/2015 | Basu | A61B 5/02433 600/323 |
| 2016/0007409 A1* | 1/2016 | Shibuya | H04W 88/02 455/95 |
| 2016/0128179 A1* | 5/2016 | Okamoto | H05K 1/0268 361/760 |
| 2017/0065228 A1* | 3/2017 | Hirano | A61B 5/721 |
| 2018/0068942 A1* | 3/2018 | Shibuya | H01L 23/66 |
| 2018/0323140 A1* | 11/2018 | Shibuya | H01L 23/49838 |

* cited by examiner

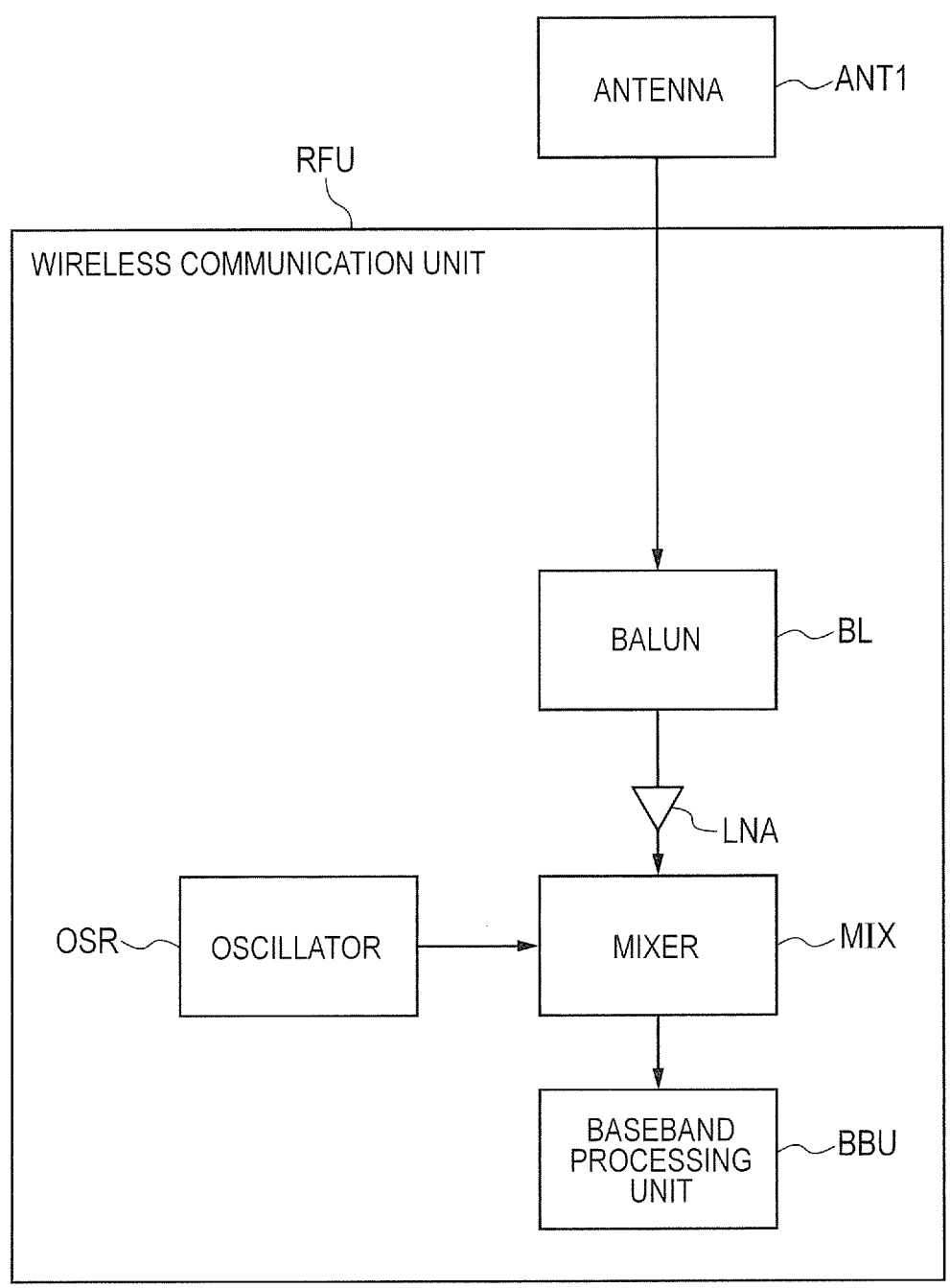

ELECTRONIC APPARATUS

CROSS-REFERENCE TO RELATED APPLICATIONS

The disclosure of Japanese Patent Application No. 2015-239628 filed on Dec. 8, 2015 including the specification, drawings and abstract is incorporated herein by reference in its entirety.

BACKGROUND

The present invention relates to an electronic apparatus and pertains to a technology that is effective for application to, for example, an electronic apparatus constituent in a wireless communication system.

Japanese Unexamined Patent Application Publication No. 2001-245860 (Patent Document 1) describes a technology that installs a pulse wave sensor onto an eyeglass frame.

Japanese Unexamined Patent Application Publication No. 2006-312010 (Patent Document 2) describes a technology in which a sensor node having a wireless communication function is equipped with a pulse wave sensor to detect biological information.

RELATED ART DOCUMENTS

Patent Documents

[Patent Document 1]
Japanese Unexamined Patent Application Publication No. 2001-245860
[Patent Document 2]
Japanese Unexamined Patent Application Publication No. 2006-312010

SUMMARY

"Bluetooth (a registered trademark) Low Energy" (which will be referred to as BLE hereinafter) is considered to be promising as a major communication scheme in Internet of Things (IoT) which is expected to grow. For example, sensor nodes in which this "BLE" is combined with a variety of sensors are developed actively.

In particular, for a sensor node incorporating a biosensor to detect biological information, downsizing the node is hoped for from a size of a "comfortable" level to a size of an "unaware" level in consideration of biological burden reduction. Furthermore, improvement in the accuracy of detection made by a biosensor is hoped for to make effective use of biological information detected by the biosensor. Meanwhile, a sensor node has a wireless communication function and a sensor node structure enabling to ensure a good communication quality is hoped for.

Other problems and novel features will be apparent from the description in the present specification and the attached drawings.

In an electronic apparatus according to one embodiment, a sensor section with a biosensor formed therein and a main body section with a data processing unit and a wireless communication unit formed therein are separated. The sensor section includes an A/D converter unit that converts an analog signal corresponding to biological information detected by the pulse wave sensor to a digital signal. Digital signal transmission is performed from the A/D converter unit to the data processing unit.

According to one embodiment, it can be accomplished to downsize a sensor node incorporating a biosensor to detect biological information. According to one embodiment, it can also be accomplished to improve the accuracy of detection made by the biosensor. According to one embodiment, furthermore, a good communication quality can be ensured.

BRIEF DESCRIPTION OF THE DRAWINGS

FIG. 6 is a block diagram principally depicting an example of a detailed configuration of a receiver section of the wireless communication unit included in a sensor node;

DETAILED DESCRIPTION

Figure 1:
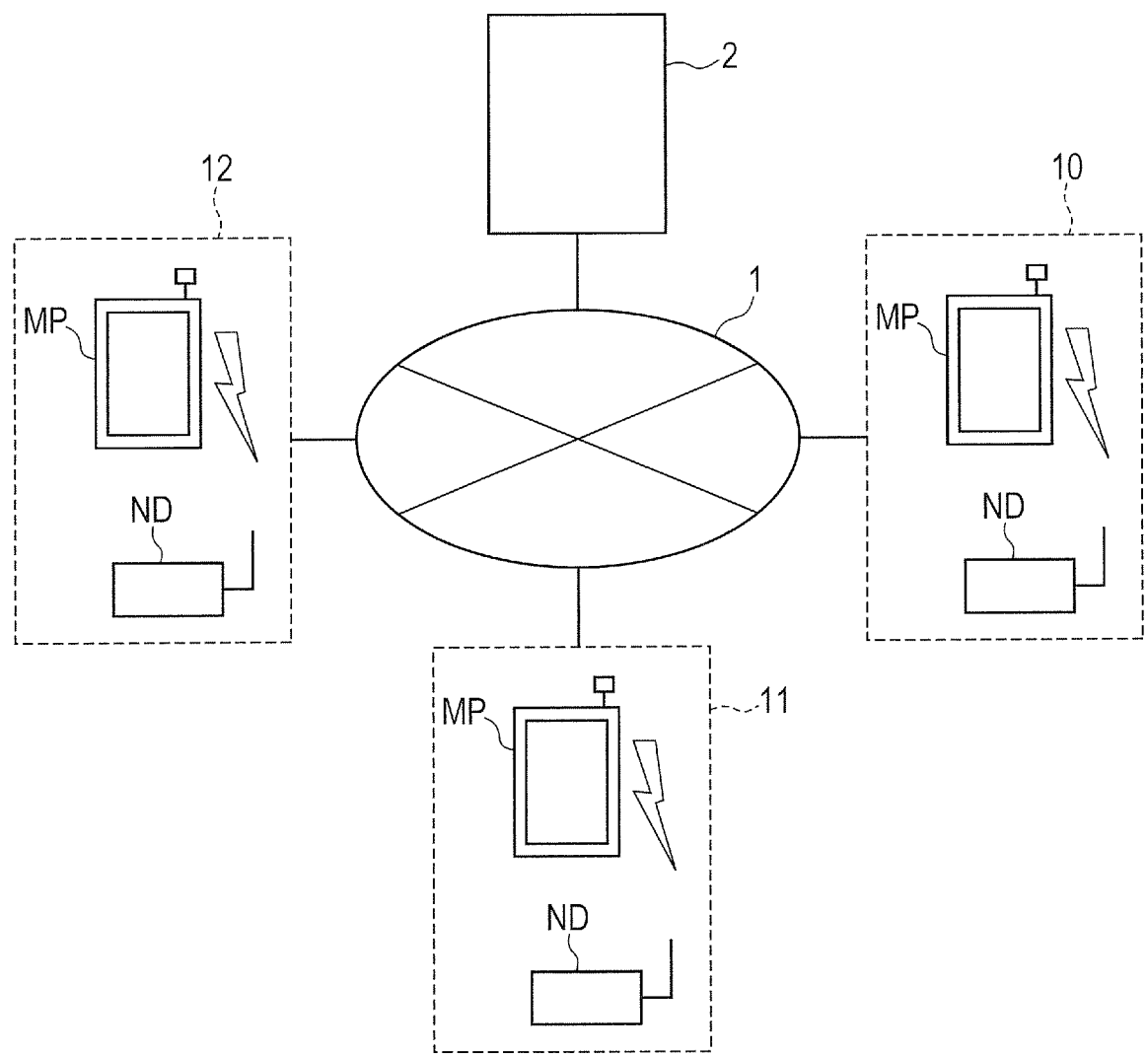
FIG. 1 is a schematic diagram depicting an example of architecture of a wireless communication system configured through combination of a sensor node that uses "BLE" with a smartphone.

In the following description of an embodiment, the embodiment is divided into plural sections or embodiments, when necessary for convenience sake, and these sections or embodiments are described; they are not independent of each other, unless otherwise specified, and they relate to one another such that one is an example of modification to another or detailed description, supplementary description, or the like, of another in part or whole.

Besides, in the following description of an embodiment, where the number of elements among others (including the number of pieces, a numeric value, quantity, range, etc.) is mentioned, that number should not be limited to a particular number mentioned and may be more or less than the particular number, unless otherwise specified and unless that number is, in principle, obviously limited to the particular number.

Furthermore, for an embodiment which will be described below, needless to say, its components (including constituent steps or the like) are not always necessary, unless otherwise specified and unless such components are, in principle, considered to be necessary obviously.

Likewise, in an embodiment which will be described below, when the shape of a component or the like, a positional relation between components, etc. are described, such description should be construed to include those that are substantially similar or analogous to the shape, etc., unless otherwise specified and unless such description is, in principle, considered to be obviously exclusive. This is also true for the above-mentioned numeric value and range.

Moreover, in all the drawings to explain an embodiment, corresponding members are, in principle, assigned identical reference designators and their repeated description is omitted. And now, to make a drawing easy to understand, even a planar representation may include a hatched portion.

Embodiment

<Architecture of a Wireless Communication System>

"BLE" is one of extended specifications of "Bluetooth", a short-range wireless communication technology and it is a technology enabling wireless communication with extremely low electric power. The "BLE" enables communication at a maximum rate of 1 Mbps using radio waves in a 2.4 GHz band which can be used without a license. A chip adapted for "BLE" is able to operate with power on the order of one-third of power that has heretofore been required and is supposed to be operable over several years even with a miniature battery. That is, unlike traditional "Bluetooth", "BLE" is suitable for application in which driving continues for a long time with a miniature battery. Recently, there is increasing usage of a wearable device that is very small and light, such as a biosensor, and that is linked to a smartphone. For instance, linking a variety of sensors, such as an incoming call detector, clock time instrument, blood pressure monitor, thermometer, heart rate meter, pulse wave meter to a smartphone using "BLE" is considered. In such a wireless communication system, it is possible to grasp conditions of a human body by acquiring and analyzing information from sensors using a smartphone. That is, by combining sensors that use "BLE" with a smartphone, it is enabled to monitor information on a human body and a promising application for management of the health of a human body through monitoring information on a human body is expected.

FIG. 1 is a schematic diagram depicting an example of architecture of a wireless communication system configured through combination of a sensor node that uses "BLE" with a smartphone. In FIG. 1, for example, a personal unit 10 dedicated for each individual person includes a smartphone MP and a sensor node ND that can be attached to a human body. The smartphone MP and the sensor node ND are linked by "BLE". This allows the personal unit 10 to transmit, e.g., biological information detected by the sensor node ND to the smartphone MP by "BLE" and, thereby, management of the health of an individual person based on the biological information can be performed. In this way, by linking a sensor node ND and a smartphone MP by "BLE" in a single personal unit 10, it is possible to implement a typical application for management of the health of an individual person.

However, a wireless communication system is not so limited. For instance, as depicted in FIG. 1, by coupling smartphones MPs respectively included in plural personal units 10 through 12 to a server 2 over a network, it is also possible for the server 2 to carry out biological information collection and utilization (such as providing a service based on biological information).

<Configuration of a Sensor Node>

Figure 2:
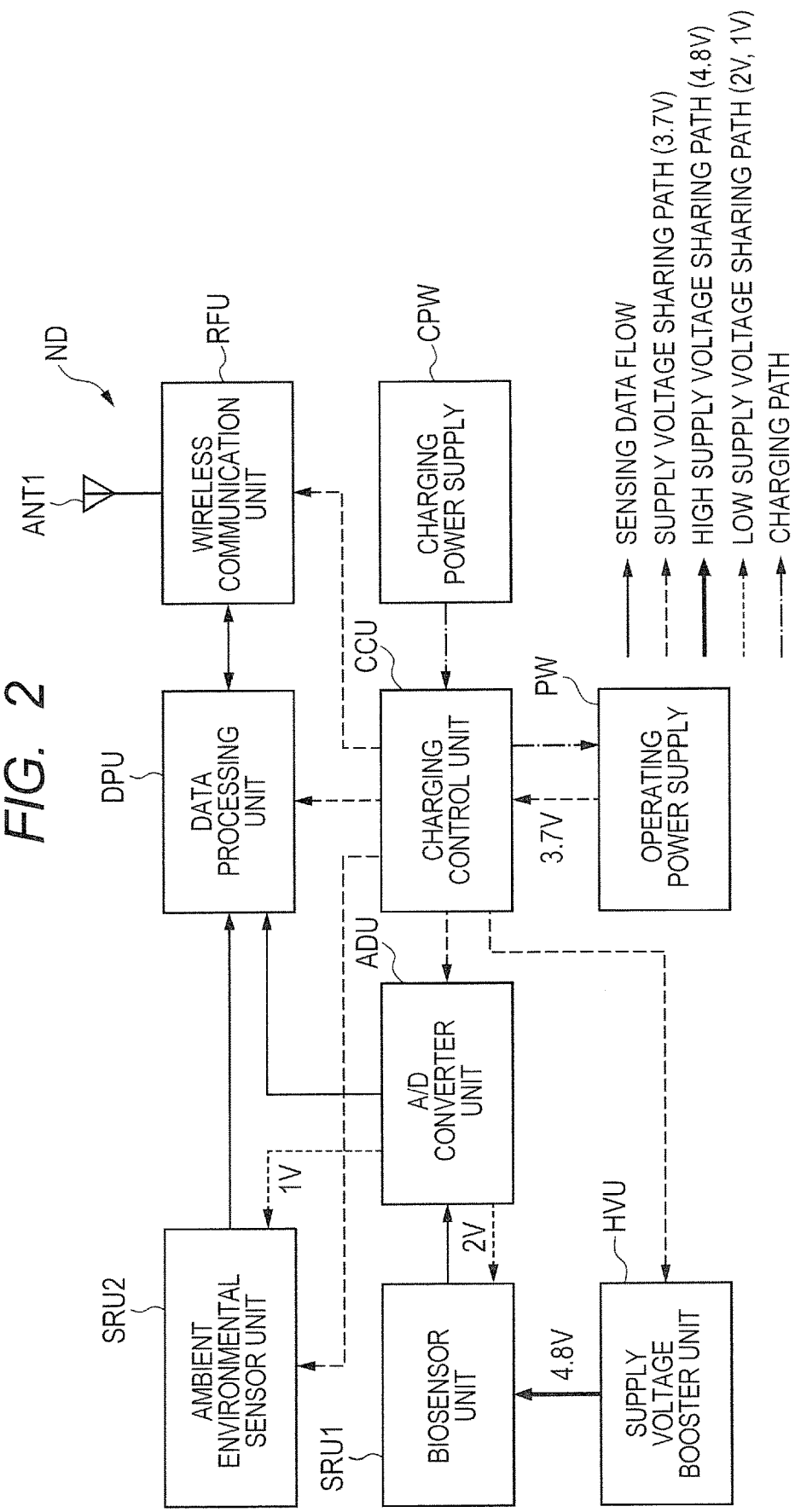
FIG. 2 is a functional block diagram depicting a functional configuration of a sensor node according to an embodiment.

Descriptions are then provided about a functional configuration of a sensor node constituent in a wireless communication system. FIG. 2 is a functional block diagram depicting a functional configuration of a sensor node ND according to the present embodiment. As depicted in FIG. 2, a sensor node ND according to the present embodiment includes an operating power supply PW, a charging control unit CUU, a biosensor unit SRU1, an ambient environmental sensor unit SRU2, a data processing unit (signal processing unit) DPU, a wireless communication unit RFU, an antenna ANT1, an A/D converter unit ADU, and a supply voltage booster unit HVU. This sensor node ND is configured to be chargeable by a charging power supply CPW which is supplied externally.

The operating power supply PW is configured of, e.g., a chargeable/dischargeable lithium ion battery. This operating power supply PW is configured to be chargeable under control of the charging control unit CCU by coupling the charging power supply CPW provided outside the sensor node ND to the charging control unit CCU within the sensor node ND. Furthermore, the operating power supply PW supplies an operating voltage (e.g., about 3.7 V) to the charging control unit CCU and this operating voltage is supplied from the charging control unit CCU to the data processing unit DPU, wireless communication unit RFU, ambient environmental sensor unit SRU2, A/D converter unit ADU, and supply voltage booster unit HVU.

The biosensor unit SRU1 is configured to be attachable to a living body and configured to detect biological information. This biosensor unit SRU1 is configured so that it can detect highly accurate biological information and comprised of, e.g., a highly accurate pulse wave sensor to detect the pulse waves of a living body and a highly accurate temperature sensor to detect the temperature of a living body among others.

The ambient environmental sensor unit SRU2 is comprised of sensors or the like for sensing an external environment where the sensor node ND is situated and includes, e.g., an acceleration sensor to detect acceleration that is applied to the sensor node ND, a gyroscope to detect an angular velocity that is applied to the sensor node ND, a temperature sensor to detect an ambient temperature of the sensor node ND, a microphone to detect sound, etc.

The A/D converter unit ADU has a function of taking input of an analog signal corresponding to biological information detected by the biosensor unit SRU1 and converting the analog signal to a digital signal and is configured to output a digital signal resulting from the conversion to the data processing unit DPU. The A/D converter unit ADU is also configured to lower an operating voltage supplied from the charging control unit CCU, thus generating a first low voltage (about 2 V) and a second low voltage (about 1 V), and supply the first low voltage to the biosensor unit SRU1 as well as supply the second low voltage to the ambient environmental sensor unit SRU2.

The power supply booster unit HVU is configured to boost an operating voltage supplied from the charging control unit CCU, thus generating a high voltage (about 4.8 V), and supply this high voltage to the biosensor unit SRU1 and is configured of, e.g., a DC/DC converter.

The data processing unit DPU is configured to take input of a digital signal resulting from conversion made by the A/D converter unit ADU, take input of a signal that is output from the ambient environmental sensor unit SRU2, and perform data processing with these signals. The data processing unit DPU is also configured to output a signal resulting from the data processing to the wireless communication unit RFU. Moreover, the data processing unit DPU is configured to take input of a received signal received by the wireless communication unit RFU and perform data processing with the received signal.

The wireless communication unit RFU is configured to take input of a signal resulting from data processing by the data processing unit DPU and generate a transmission signal conforming to "BLE". A transmission signal generated by the wireless communication unit RFU is delivered to the antenna ANT1 and transmitted from the antenna ANT1. The wireless communication unit RFU is also configured to convert a received signal received by the antenna ANT1 and output a resulting signal to the data processing unit DPU.

Figure 3:
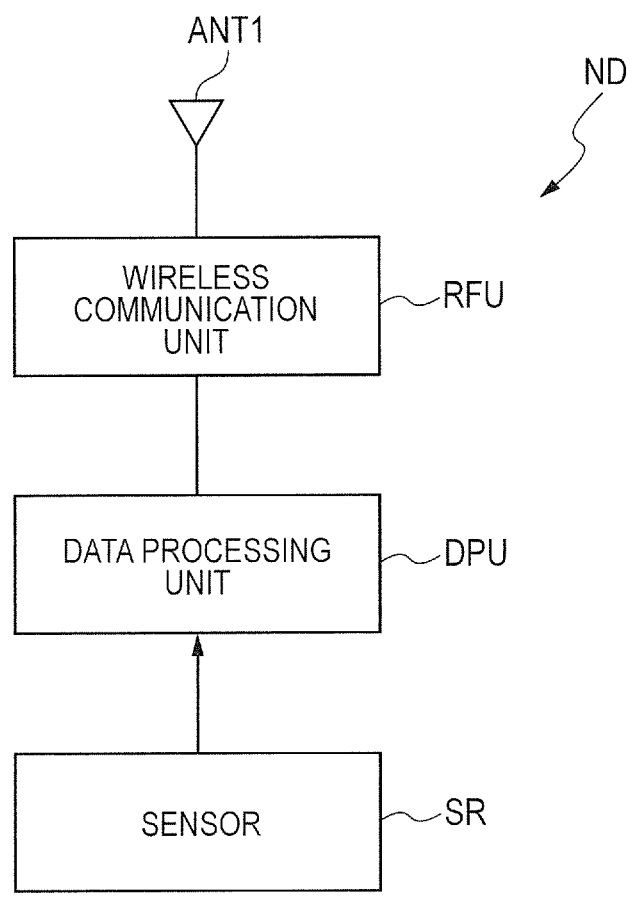
FIG. 3 is a functional block diagram depicting a functional configuration of the sensor node according to the embodiment.

To summarize the above-described configuration, a sensor node ND is equipped with a sensor SR, a data processing unit DPU, a wireless communication unit RFU, and an antenna (for communication) ANT1, as is depicted in FIG. 3. The sensor SR is configured of an element or a device to detect a physical quantity and its variation of temperature, pressure, flow rate, light, magnetism, or the like and is configured to convert a detected quantity to a suitable signal and output that signal. As this sensor SR, for example, a pulse wave sensor, a temperature sensor, a pressure sensor, a flow rate sensor, an optical sensor, a magnetic sensor, an illuminance sensor, an acceleration sensor, an angular velocity sensor, or an image sensor, etc. may be included.

The data processing unit DPU is configured to process an output signal which has been output from the sensor SR and output processed data. Moreover, the wireless communication unit RFU is configured to convert data processed by the data processing unit DPU to a signal with a radio frequency and transmit that signal from the antenna ANT1. Moreover, the wireless communication unit RFU is also configured to receive a signal with a radio frequency via the antenna ANT1.

In the sensor node ND thus configured, when a physical quantity is detected by the sensor SR, a signal is output from the sensor SR and this output signal is input to the data processing unit DPU. Then, the data processing unit DPU processes the input signal and processed data is output to the wireless communication unit RFU. Subsequently, the wireless communication unit RFU converts the input data to a radio frequency signal and the radio frequency signal is transmitted from the antenna ANT1. In this way, based on a physical quantity detected by the sensor SR, a radio frequency signal corresponding to this physical quantity is to be transmitted at the node.

<Detailed Configuration of a Sensor Node>

Figure 4:
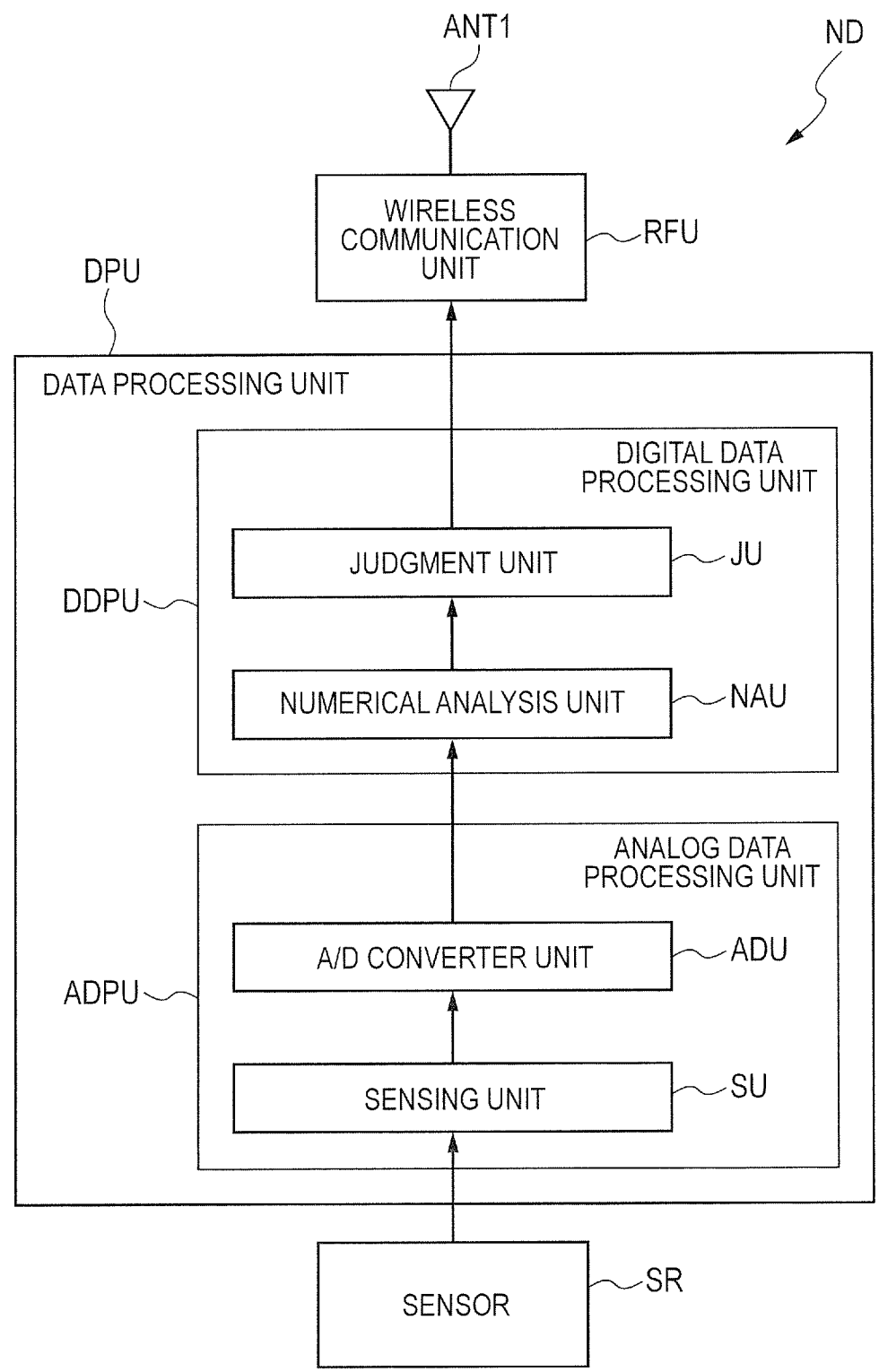
FIG. 4 is a block diagram principally depicting an example of a detailed configuration of a data processing unit included in a sensor node.

Further descriptions are provided about one example of a detailed configuration of a sensor node. FIG. 4 is a block diagram principally depicting an example of a detailed configuration of the data processing unit DPU included in a sensor node. As depicted in FIG. 4, the data processing unit DPU included in a sensor node is comprised of an analog data processing unit ADPU and a digital data processing unit DDPU. The analog data processing unit ADPU is configured to include a sensing unit SU and an A/D converter unit ADU and the digital data processing unit DDPU is configured to include a numerical analysis unit NAU and a judgment unit JU.

And now, some type of sensor SR outputs a digital signal. In this case, the analog data processing unit ADPU is dispensed with as a part of the data processing unit DPU and the DPU can also be configured entirely of the digital data processing unit DDPU. In this case, the analog data processing unit ADPU is to be incorporated in the sensor SR. However, since the present embodiment is aimed at downsizing the sensor SR, it is not assumed that the A/D converter unit ADU is incorporated in the sensor SR. On the assumption that the sensor SR and the A/D converter unit ADU are separate, descriptions are provided about an embodiment in which the data processing unit DPU is comprised of the analog data processing unit ADPU and the digital data processing unit DDPU.

To begin with, the analog data processing unit ADPU is described. The analog data processing unit ADPU is configured to take input of an analog signal which has been output from the sensor SR and convert the analog signal to data that is easy to manipulate and includes the sensing unit SU and the A/D converter unit ADU.

The sensing unit SU is, for example, configured to include an amplifier circuit, a transimpedance circuit, and a filter circuit among others. An output signal that is output from the sensor SR is minute and its signal form is often unstable for processing by the digital data processing unit DDPU. Therefore, a circuit is required to amplify a minute analog signal that is output from the sensor SR to an analog signal having an amplitude adequate for input to the digital data processing unit DDPU. Moreover, in some cases, an output signal that is output from the sensor SR may be a current instead of a voltage. In this case, the A/D converter circuit to convert an analog signal to a digital signal is only able to receive a voltage signal. For this reason, a circuit is required to convert a current signal to a voltage signal, while amplifying the signal to a voltage signal having an adequate amplitude. This circuit is called a transimpedance circuit and is an analog circuit which combines a converter circuit and an amplifier circuit. Moreover, a signal (noise) with an unwanted frequency may be mixed in an output signal from the sensor SR. In this case, noise impedes the acquisition of an output signal from the sensor. Hence, for instance, if noise has a higher frequency than an output signal, the noise has to be eliminated by a low-pass filter circuit. In contrast, if noise has lower frequency than an output signal, the noise has to be eliminated by a high-pass filter circuit.

Since it is hard to directly manipulate an output signal from the sensor, as noted above, the analog data processing unit ADPU is provided and, in the analog data processing unit ADPU, provided is the sensing unit SU including the amplifier circuit, transimpedance circuit, and filter circuit, mentioned above. A series of analog circuits making up this sensing unit SU may also be called an "analog front end (AFE)".

Then, the A/D converter unit ADU is configured to convert analog data which has been output from the sensing unit SU to digital data. That is, analog data must be converted to digital data by the A/D converter unit ADU, since the digital data processing unit DDPU can only manipulate digital data.

The digital data processing unit DDPU that follows is configured to take input of digital data which is output from the analog data processing unit ADPU and process this digital data and includes, for example, the numerical analysis unit NAU and judgment unit JU. In this context, the digital data processing unit DDPU is configured of, e.g., a microcomputer (MCU: Micro Control Unit).

The numerical analysis unit NAU is configured to take input of digital data which has been output from the analog data processing unit ADPU and perform numerical operation processing on this digital data according to a program. Then, the judgment unit JU is configured to, for example, select data to be output to the wireless communication unit RFU based on a result of numerical operation processing performed by the numerical analysis unit NAU.

The data processing unit DPU is configured as above and its operation is described below. First, a physical quantity of temperature, pressure, flow rate, light, magnetism, or the like is detected by the sensor SR and, based on a result of this detection, a weak detection signal which is an analog signal is output from the sensor SR. Then, the output weak detection signal is input to the sensing unit SU within the analog data processing unit ADPU. In the sensing unit SU, the input detection signal is amplified by the amplifier circuit. If the detection signal is a current signal, not an voltage signal, the current signal is converted to a voltage signal by the transimpedance circuit. Furthermore, to eliminate noise included in the detection signal, noise included in the detection signal is eliminated by the filter circuit. In this way, the sensing unit SU processes a detection signal (analog signal) which has been input from the sensor SR, and generates and outputs analog data (analog signal). The A/D converter unit ADU that follows takes input of analog data which has been output from the sensing circuit and converts it to digital data. Subsequently, digital data resulting from conversion made by the A/D converter unit ADU is input to the numerical analysis unit NAU within the digital data processing unit DDPU. Then, the numerical analysis unit NAU performs numerical operation processing based on the input digital data. Subsequently, based on a result of the numerical operation processing, the judgment unit JU selects digital data to be output to the wireless communication unit RFU. Then, the digital data which has been output from the digital data processing unit DDPU is input to the wireless communication unit RFU and, after converted to a radio frequency signal, it is transmitted from the antenna ANT1. In the way as above, in the sensor node, data based on a physical quantity detected by the sensor SR is generated and a radio frequency signal corresponding to this data is to be transmitted.

Figure 5:
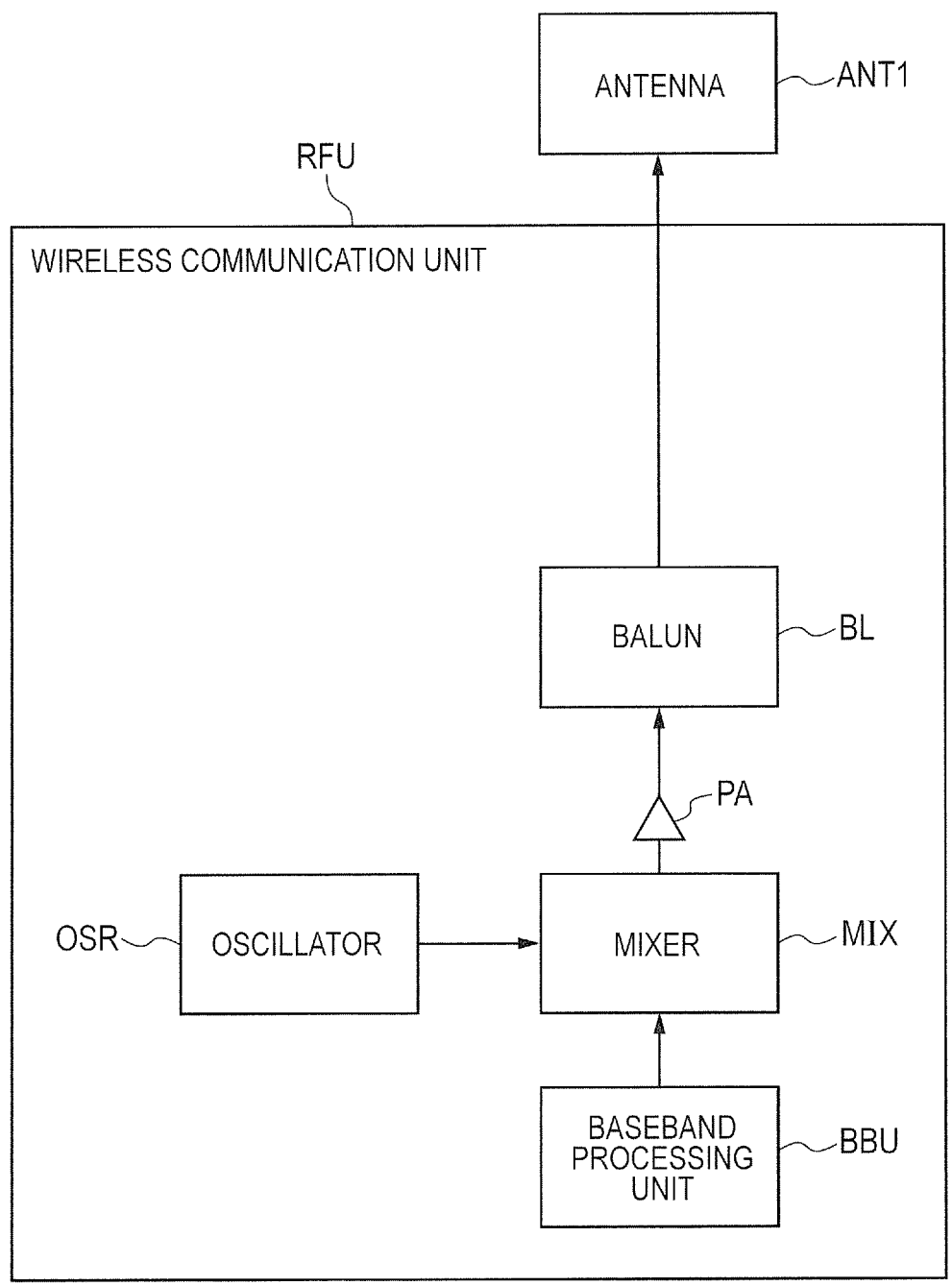
FIG. 5 is a block diagram principally depicting an example of a detailed configuration of a transmitter section of a wireless communication unit included in a sensor node.

Descriptions are then provided about an example of a detailed configuration the wireless communication unit RFU included in a sensor node. FIG. 5 is a block diagram principally depicting an example of a detailed configuration of a transmitter section of the wireless communication unit RFU included in a sensor node. In FIG. 5, the wireless communication unit RFU includes a baseband processing unit BBU, a mixer MIX, an oscillator OSR, a power amplifier PA, and a balun BL.

The baseband processing unit BBU is configured to generate a baseband signal for modulation from digital data and pass that signal for further processing. The oscillator OSR is configured to generate a radio frequency carrier. Moreover, the mixer MIX is configured to generate a radio frequency signal by superimposing the baseband signal generated by the baseband processing unit BBU on the carrier generated by the oscillator OSR. Furthermore, the power amplifier PA is configured to amplify the radio frequency signal which is output from the mixer MIX. The balun BL is an element to convert between balanced and unbalanced electric signals.

The transmitter section of the wireless communication unit RFU is configured as above and its operation is described below. First, in the baseband processing unit BBU, a baseband signal for modulation is generated from digital data which has been input from the data processing unit. Then, this baseband signal is modulated by being mixed with a carrier generated by the oscillator OSR in the mixer MIX and a radio frequency signal is generated. After being amplified by the power amplifier PA, this radio frequency signal passes through the balun BL and is output from the wireless communication unit RFU. Subsequently, the radio frequency signal which has been output from the wireless communication unit RFU is transmitted from the antenna ANT1 which is electrically coupled to the wireless communication unit RFU. In the way as above, a radio frequency signal can be transmitted from a sensor node.

In turn, FIG. 6 is a block diagram principally depicting an example of a detailed configuration of a receiver section of the wireless communication unit RFU included in a sensor node. In FIG. 6, the wireless communication unit RFU includes a baseband processing unit BBU, a mixer MIX, an oscillator OSR, a low noise amplifier LNA, and a balun BL.

The balun BL is an element to convert between balanced and unbalanced electric signals. Moreover, the low noise amplifier LNA is configured to amplify a received weak signal. The oscillator OSR is configured to generate a radio frequency carrier. The mixer MIX is configured to generate a baseband signal by superimposing the received signal amplified by the low noise amplifier LNA on the carrier generated by the oscillator OSR. The baseband processing unit BBU is configured to generate digital data from a demodulated baseband signal and pass the digital data for further processing.

The receiver section of the wireless communication unit RFU is configured as above and its operation is described below. First, a received signal received by the antenna ANT1 passes through the balun BL and is input to the low noise amplifier LNA and amplified. Subsequently, the amplified received signal is mixed with the carrier generated by the oscillator OSR in the mixer MIX and a baseband signal is thus generated. Then, the baseband signal demodulated is converted to digital data in the baseband processing unit BBU and passed for further processing. In the way as above, a received signal can be received at a sensor node.

<Principle of how a Pulse Wave Sensor Makes Detection>

In the present embodiment, as a biosensor to detect biological information, for example, a pulse wave sensor is assumed. Accordingly, a mechanism of how this pulse wave sensor makes detection is described below.

Figure 7A:
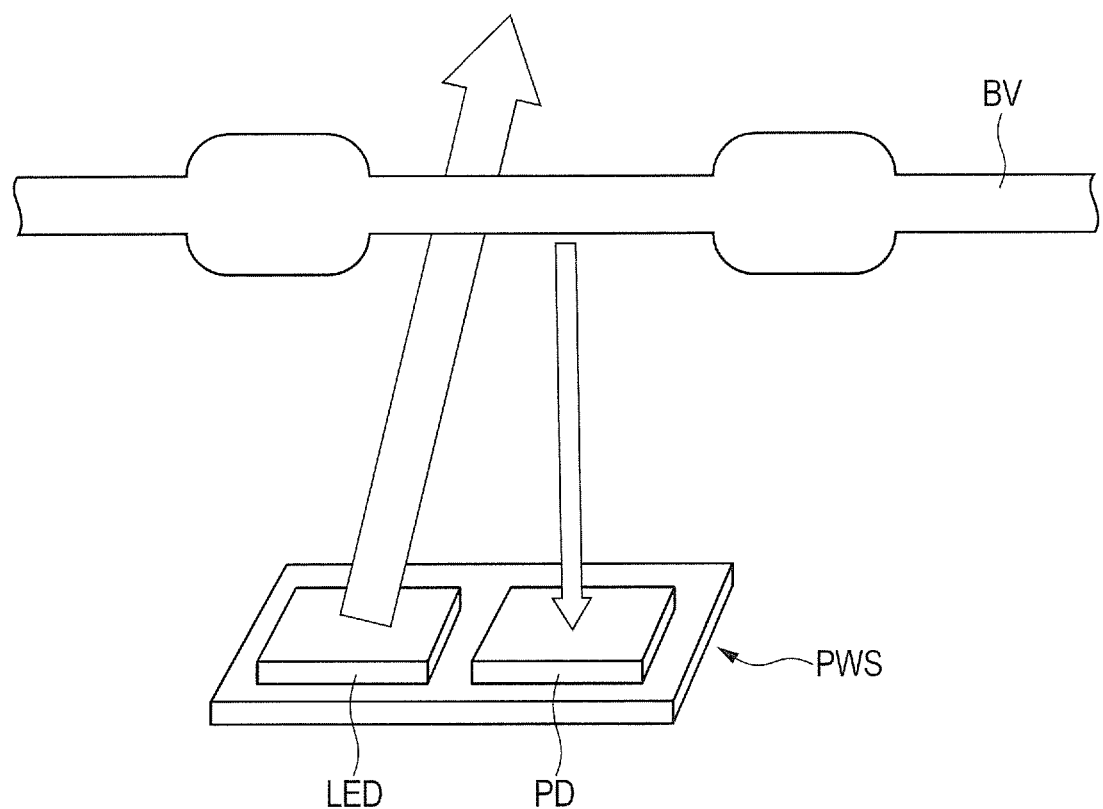
FIG. 7A is a schematic diagram to explain the principle of how a pulse wave sensor makes detection and FIG. 7B is a diagram depicting one example of a waveform detected by the pulse wave sensor.
Figure 7B:
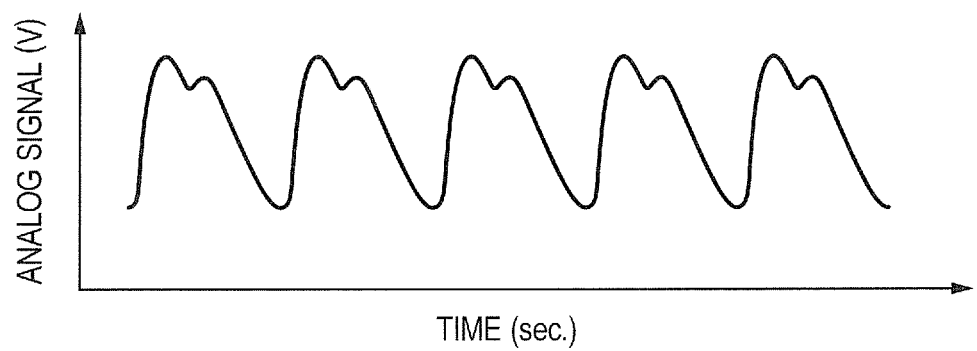

FIGS. 7A and 7B are diagrams provided to explain a principle of how the pulse wave sensor makes detection. FIG. 7A is a schematic diagram to explain the principle of how the pulse wave sensor makes detection and FIG. 7B is a diagram depicting one example of a waveform detected by the pulse wave sensor. First, in FIG. 7A, a blood vessel (arterial) BV inside a living body is depicted and the pulse wave sensor PWS is placed to touch the living body. The pulse wave sensor PWS includes, for example, a light-emitting diode LED which emits green light and a photodiode PD which receives reflected light from the blood vessel BV. The principle of how the pulse wave sensor PWS thus configured makes detection is described. In FIG. 7A, there is a pulse wave in the living body. This pulse wave represents a periodic change in the inner volume of the blood vessel BV occurring, as the heart delivers blood. Therefore, when the blood vessel BV is irradiated with green light from the light-emitting diode LED included in the pulse wave sensor PWS, for example, as depicted in FIG. 7A, the amount of incident light received by the blood vessel BV changes in response to the periodic change in the inner volume of the blood vessel, resulting in a periodic change in the intensity of the reflected light from the blood vessel. The photo diode PD included in the pulse wave sensor PWS detects this periodic change in the intensity of the reflected light; in this way, the pulse wave can be detected.

FIG. 7B is a diagram schematically depicting an analog signal which is output from the photo diode PD incorporated in the pulse wave sensor PWS. As depicted in FIG. 7B, it can be seen that the analog signal has a periodic waveform corresponding to the pulse wave. Therefore, by analyzing this analog signal, biological information on the pulse wave of a living body can be obtained.

<Implementation Structure of a Sensor Node>

Figure 8:
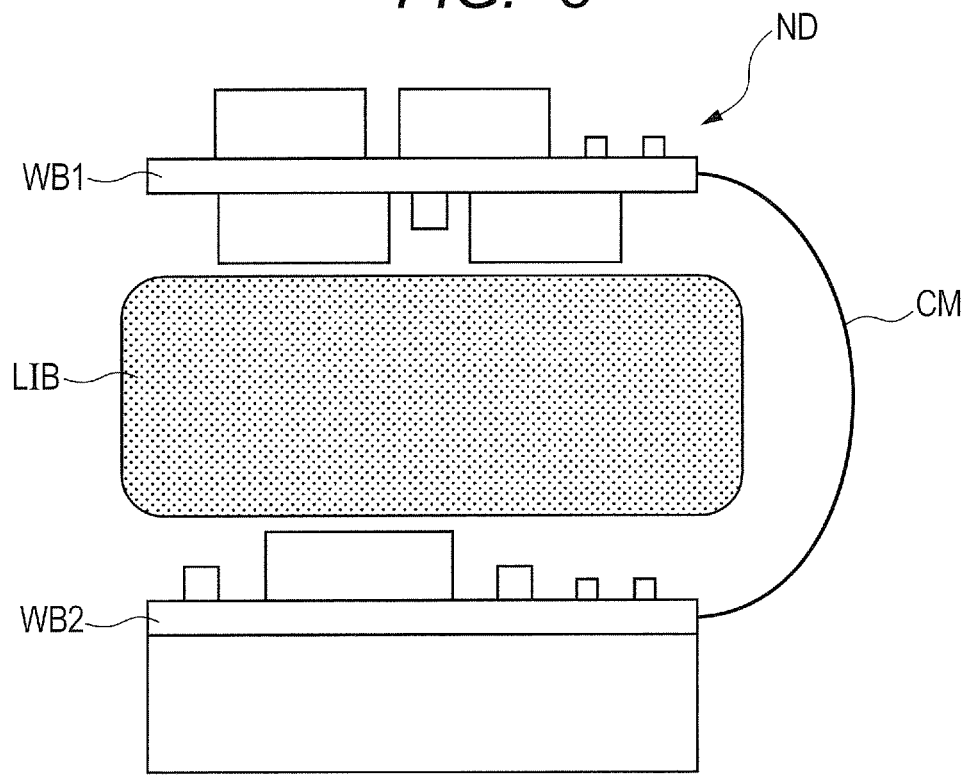
FIG. 8 is a schematic diagram depicting a schematic implementation structure of the sensor node according to the embodiment.

Descriptions are then provided about an implementation structure of a sensor node (electronic apparatus) ND according to the present embodiment. FIG. 8 is a schematic diagram depicting a schematic implementation structure of the sensor node ND according to the present embodiment. As depicted in FIG. 8, the sensor node ND according to the present embodiment includes a wring board WB1 and a wiring board WB2 and electronic components are mounted on the wring boards WB1 and WB2, respectively. And, a lithium ion battery LIB is placed, sandwiched between the wring boards WB1 and WB2, as depicted in FIG. 8. The wring boards WB1 and WB2 are electrically coupled to each other, for example, by a conductive member CM.

<<Attachment of a Sensor Node>>

Figure 9:
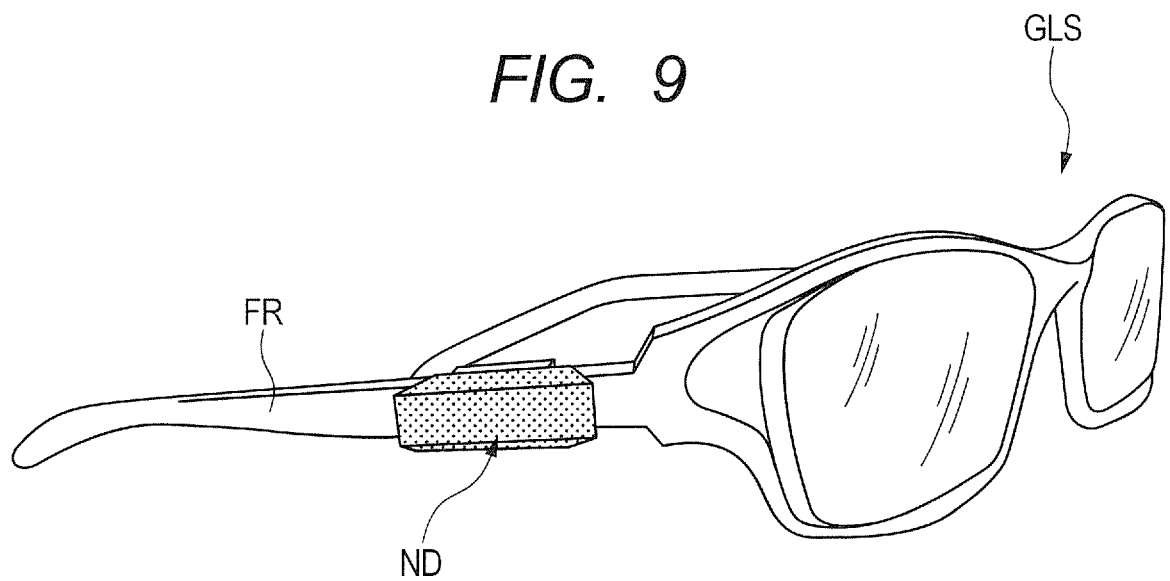
FIG. 9 is a diagram depicting a state in which the sensor node according to the embodiment was attached onto an eyeglass frame of a pair of glasses.

The sensor node ND is assumed to be placed in a position where it can touch a living body. In the present embodiment, for example, the sensor node ND is assumed to be attached onto an eyeglass frame. FIG. 9 is a diagram depicting a state in which the sensor node ND according to the present embodiment was attached onto the eyeglass frame FR of a pair of glasses GLS. In particular, the sensor node ND is installed in a position on the eyeglass frame FR, the position corresponding to a "temple" portion of a human body, since the pulse wave sensor is incorporated in the sensor node ND according to the present embodiment and pulse wave detection is made by this pulse wave sensor.

By installing the sensor node ND according to the present embodiment onto the eyeglass frame FR in this way, it is possible to accommodate intended uses mentioned below. That is, by setting the pulse wave sensor incorporated in the sensor node to touch the "temple" portion of a human body, it is possible to detect a pulse wave and measure an amount of activity of the human body. Alternatively, by an acceleration sensor which may be incorporated in the sensor node ND, it is possible to grasp movement of the head portion of a human body and alert for drowsy driving with a smartphone from information relevant to acceleration corresponding to the movement of the head portion. Furthermore, by monitoring a temperature sensor to detect bodily temperature and a temperature sensor to detect outside air temperature, which may be incorporated in the sensor node ND, it is possible to alert for a heatstroke with a smartphone based on information on, inter alia, a temperature difference between the bodily temperature and the outside air temperature. Moreover, by aggregating information obtained from the pulse wave sensor, acceleration sensor, and temperature sensors which may be incorporated in the sensor node ND, it is also possible to apply the sensor node to watching for an old person and detecting and notifying if the old person has fallen down flat. Moreover, by incorporating a microphone to collect sound into the sensor node ND, it is also possible to apply the sensor node to measure an amount of utterance. It will be understood that, by installing the sensor node ND according to the present embodiment onto the eyeglass frame FR in this way, the sensor node can be made applicable to a variety of intended uses and highly beneficial. Therefore, it is needed to make the sensor node ND according to the present embodiment so small that it can be installed onto the eyeglass frame FR. To meet this requirement, the present embodiment realizes such downsizing of the sensor node ND, while achieving a high accuracy of detection by the sensor node ND, which makes the sensor node ND highly beneficial. In the following, descriptions are provided about a detailed implementation structure of the sensor node ND embodied on the assumption that the sensor node ND according to the present embodiment is installed onto, e.g., the eyeglass frame FR.

<<Detailed Implementation Structure>>

Figure 10:
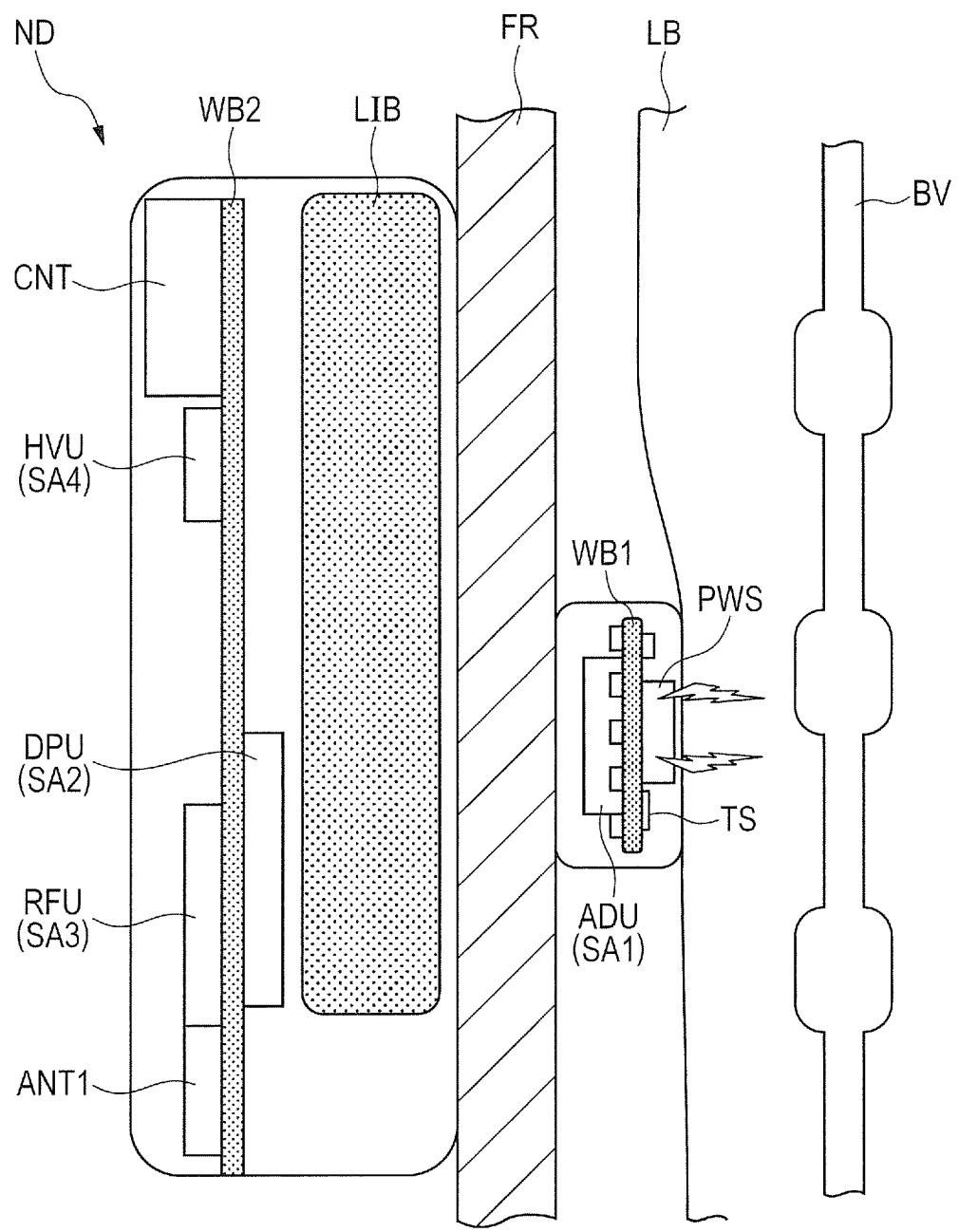
FIG. 10 is a schematic diagram depicting an internal structure of a sensor node, assuming the state in which the sensor node according to the embodiment was attached onto an eyeglass frame.

FIG. 10 is a schematic diagram depicting an internal structure of a sensor node ND, assuming the state in which the sensor node ND according to the present embodiment was attached onto an eyeglass frame. As depicted in FIG. 10, the sensor node ND according to the present embodiment is installed onto the eyeglass frame FR and roughly separated into two constituent elements. In other words, the sensor node ND according to the present embodiment includes two constituent elements which are separated from each other and the sensor node ND is installed onto the eyeglass frame FR so as to sandwich the eyeglass frame FR between these two constituent elements.

In FIG. 10, one of the two constituent elements making up the sensor node ND is sandwiched between the eyeglass frame FR and a human body LB and placed so as to touch the human body LB. In this instance, a blood vessel BV existing inside the human body LB is depicted in FIG. 10.

First, one of the two constituent elements making up the sensor node ND, a constituent element which touches the human body LB includes the wiring board WB1 and, on the surface (the right side, as depicted in FIG. 10) of this wiring board WB1, a pulse wave sensor PWS to detect a pulse wave and a temperature sensor TS to detect bodily temperature are mounted. Here, the height of the pulse wave sensor PWS from the surface of the wiring board WB1 is higher than the height of the temperature sensor TS from the surface of the wiring board WB1. More specifically, the height of the pulse wave sensor PWS from the surface of the wiring board WB1 is highest among electronic components mounted on the surface of the wiring board WB1. Consequently, the pulse wave sensor PWS is configured to be allowed to touch the human body LB.

In contrast, on the rear surface (the left side, as depicted in FIG. 10) of the wiring board WB1, a semiconductor apparatus SA1 serving as the A/D converter unit ADU is mounted. That is, on both the surfaces of the wiring board WB1, electronic components (a semiconductor component) are to be mounted. As noted above, the wiring board WB1 includes the pulse wave sensor PWS which is mounted on the surface and is to detect a pulse wave (biological information) and the semiconductor apparatus SA1 which is mounted on the rear surface and serves as the A/D converter unit ADU to convert an analog signal corresponding to a pulse wave detected by the pulse wave sensor PWS to a digital signal.

Then, in FIG. 10, a constituent element, the other one of the two constituent elements making up the sensor node ND, is placed on the outer side of the eyeglass frame FR. This constituent element includes the wiring board WB2 and, on the surface (the left side, as depicted in FIG. 10) of this wiring board WB2, a connector CNT, a semiconductor apparatus SA4 serving as the booster unit HVU, a semiconductor apparatus SA3 serving as the wireless communication unit RFU, and the antenna ANT1 are mounted. In contrast, on the rear surface (the right side, as depicted in FIG. 10) of the wiring board WB2, a semiconductor apparatus SA2 serving as the data processing unit DPU which takes input of a digital signal which has been output from the A/D converter unit ADU and processes that signal is mounted. Furthermore, a chargeable/dischargeable lithium ion battery LIB is placed, sandwiched between the wiring board WB2 and the eyeglass frame FR. The connector CNT mounted on the surface of the wiring board WB2 is electrically coupled to the lithium ion battery LIB and a charging current passes through the connector CNT when the lithium ion battery LIB is charged. That is, the lithium ion battery LIB incorporated in the sensor node ND according to the present embodiment is chargeable and, when charging this lithium ion battery LIB, a charging power supply is coupled to the connector CNT and the lithium ion battery LIB is to be charged. In particular, the connector CNT in the present embodiment is compatible with a micro USB.

Moreover, the semiconductor apparatus SA4 which is mounted on the surface of the wiring board WB2 and serves as the booster unit HVU is electrically couple to the lithium ion battery LIB and, from an operating voltage that is supplied from the lithium ion battery LIB, generates a high voltage higher than the operating voltage. In particular, the semiconductor apparatus SA4 is configured of a DC/DC converter and a high voltage generated by it is supplied to the pulse wave sensor PWS mounted on the surface of the wiring board WB1 and used to activate the pulse wave sensor PWS. As noted above, the wiring board WB1 and the wiring board WB2 are electrically coupled.

As will be appreciated from the foregoing, in the sensor node ND according to the present embodiment, the wiring boards WB1 and WB2 are placed such that their rear surfaces face each other and the eyeglass frame FR and the lithium ion battery LIB are placed between the wiring boards WB1 and WB2. Here, as depicted in FIG. 10, the external size of the wiring board WB1 is smaller than the external size of the wiring board WB2. Moreover, looking at the wiring board WB2 in FIG. 10, the antenna ANT1 and the connector CNT mounted on the surface of the wiring board WB2 are placed in opposite end regions, separated farthest from each other. Moreover, the sensor node ND according to the present embodiment does not include a conductive member that planarly overlaps with the antenna ANT1. In the way as above, the sensor node ND according to the present embodiment is to be implemented and configured.

<<Planar Implementation Structure of the Wiring Board WB1>>

Figure 11A:
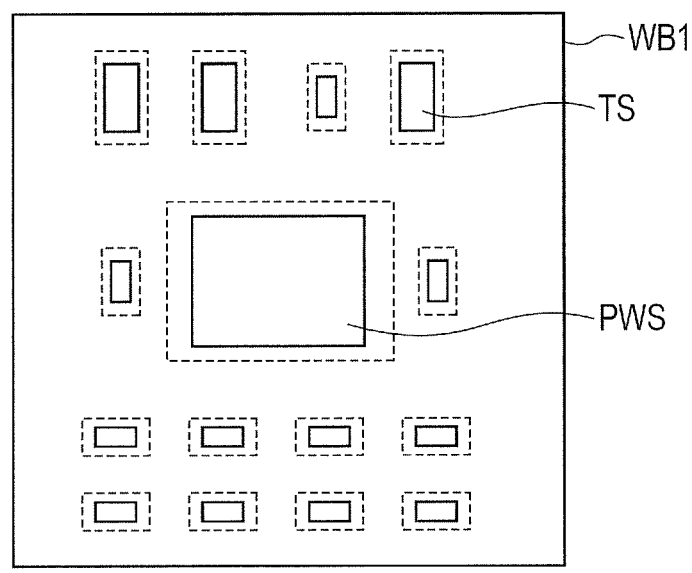
FIG. 11A is a diagram depicting an implementation structure of electronic components mounted on the surface of a first wiring board and FIG. 11B is a diagram depicting an implementation structure of electronic components mounted on the rear surface of the first wiring board.
Figure 11B:
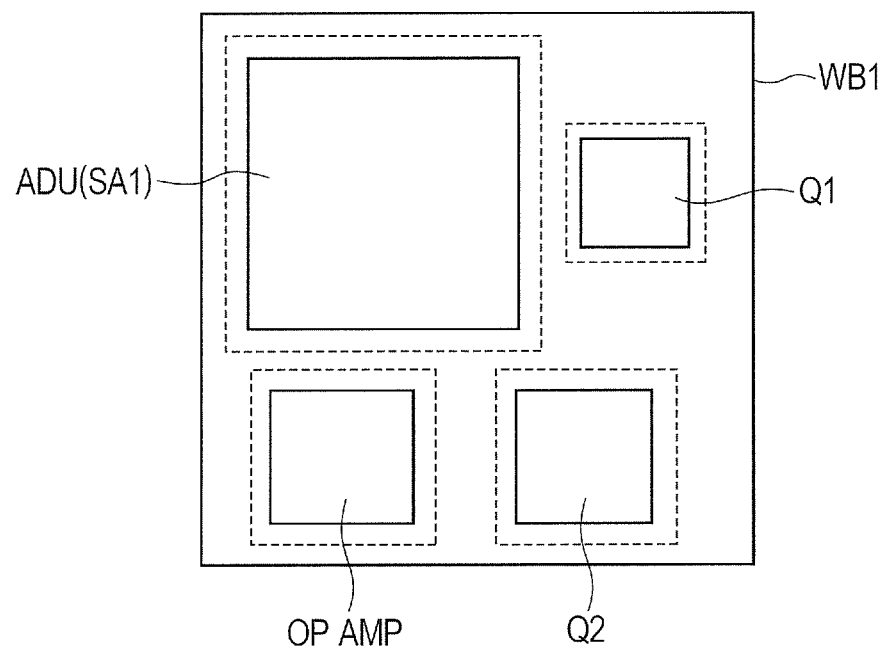

In the following, descriptions are provided about a planar implementation structure of the wiring board WB1 comprised in the sensor node ND according to the present embodiment. FIGS. 11A and 11B are schematic diagrams depicting a planar implementation structure of the wiring board WB1 constituent in the sensor node ND according to the present embodiment. In particular, FIG. 11A is a diagram depicting an implementation structure of electronic components mounted on the surface of the wiring board WB1 and FIG. 11B is a diagram depicting an implementation structure of electronic components mounted on the rear surface of the wiring board WB1.

First, as depicted in FIG. 11A, the wiring board WB1 has a substantially square shape and the pulse wave sensor PWS is mounted in its center and other electronic components including temperature sensors TS are mounted in its periphery. In contrast, as depicted in FIG. 11B, on the rear surface of the wiring board WB1, the semiconductor apparatus SA1 serving as the A/D converter unit ADU, field effect transistors Q1, Q2, and an operational amplifier OPAMP are mounted. As above, the electronic components are mounted on both the surfaces of the wiring board WB1.

<<Planar Implementation Structure of the Wiring Board WB2>>

Figure 12A:
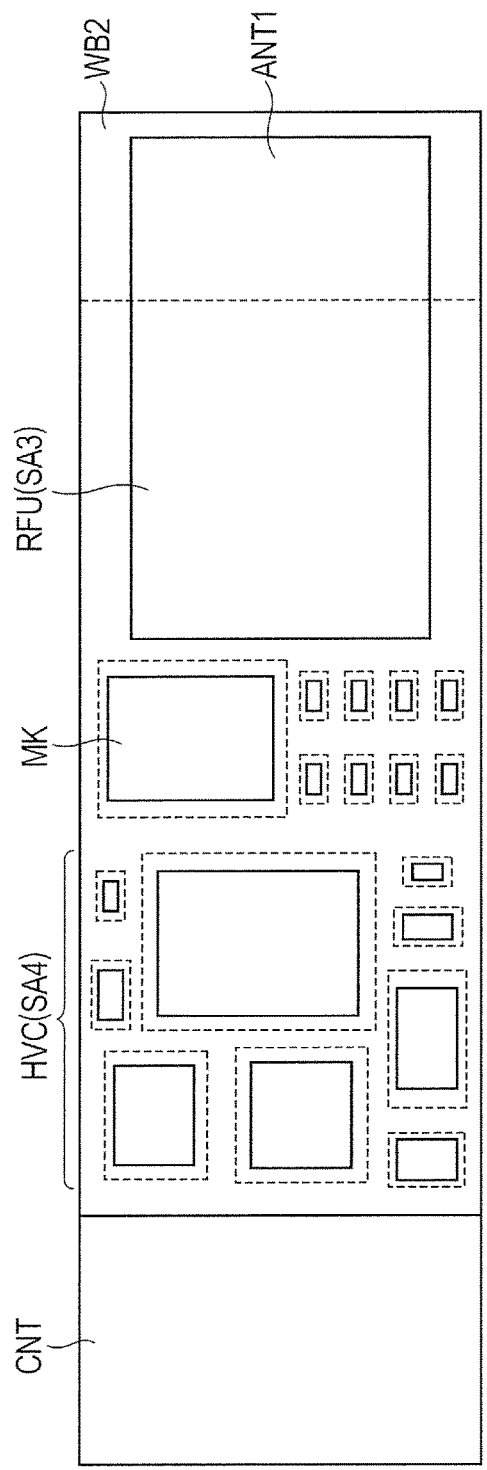
FIG. 12A is a diagram depicting an implementation structure of electronic components mounted on the surface of a second wiring board and FIG. 12B is a diagram depicting an implementation structure of electronic components mounted on the rear surface of the second wiring board.
Figure 12B:
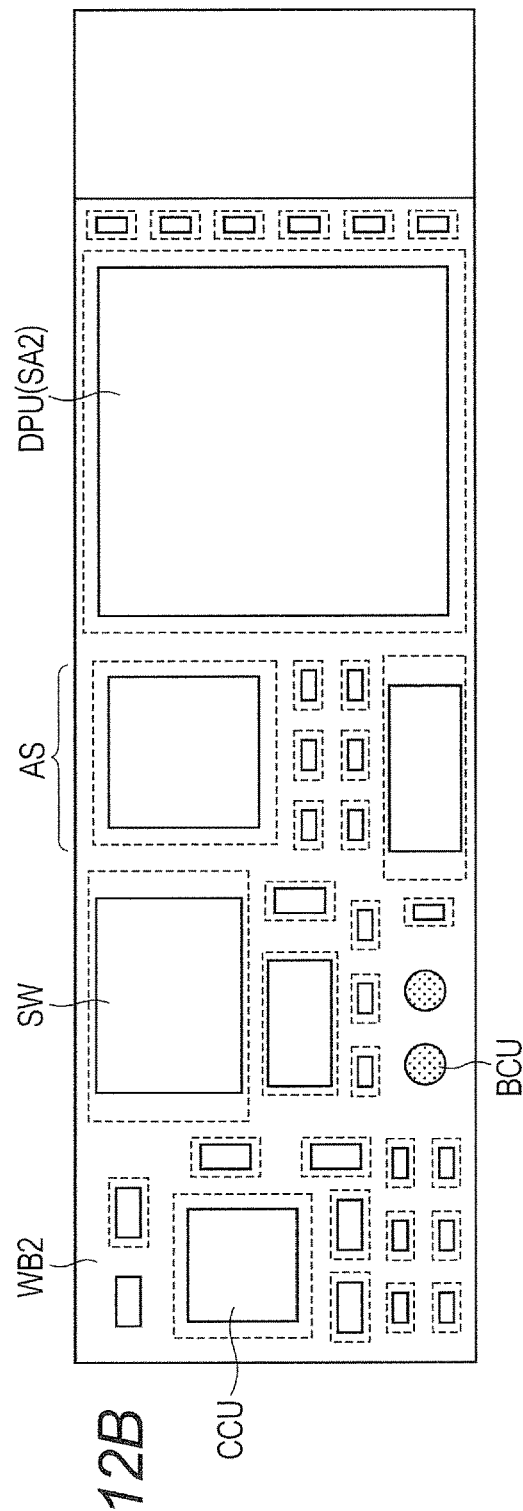

Then, descriptions are provided about a planar implementation structure of the wiring board WB2 comprised in the sensor node ND according to the present embodiment. FIGS. 12A and 12B are schematic diagrams depicting a planar implementation structure of the wiring board WB2 constituent in the sensor node ND according to the present embodiment. In particular, FIG. 12A is a diagram depicting an implementation structure of electronic components mounted on the surface of the wiring board WB2 and FIG. 12B is a diagram depicting an implementation structure of electronic components mounted on the rear surface of the wiring board WB2.

In FIG. 12A, the wiring board WB2 has a substantially rectangular shape and the connector CNT, semiconductor apparatus SA4 serving as the booster unit HVU, microphone MK having a sound collecting function, semiconductor apparatus SA3 serving as the wireless communication unit RFU, and antenna ANT1 are placed in order from the left end of the wiring board WB2. Therefore, as can be seen from FIG. 12A, the connector CNT and the antenna ANT1 are placed in opposite end regions, separated farthest from each other.

In FIG. 12B, the charging control unit CCU (semiconductor apparatus), a switch SW and a battery connection unit BCU, an acceleration sensor AS, and the semiconductor apparatus SA2 serving as the data processing unit DPU are mounted in order from the left end of the wiring board WB2. In this context, as can be seen from FIGS. 12A and 12B, a conductive member such as an electronic component is not placed in a region that planarly overlaps with the antenna ANT1. As above, the electronic components are mounted on both the surfaces of the wiring board WB2.

<Features of the Embodiment>

Then, features of the present embodiment are described. A first feature of the present embodiment resides in that the sensor node ND is comprised of the wiring boards WB1 and WB2 separated from each other, for example, as depicted in FIG. 10. Thereby, the antenna ANT1 formed on the surface of the wiring board WB2 can be situated away from the human body LB, while the pulse wave sensor PWS mounted on the surface of the wiring board WB1 is configured so that it can tough the human body LB. Accordingly, it is possible to prevent the communication characteristics of the antenna ANT1 from deteriorating due to that the antenna ANT1 is put closer to the human body and good communication characteristics can be obtained. Moreover, according to the first feature of the present embodiment, reduction of the external size of the wiring board WB1 can be accomplished by mounting the pulse wave sensor PWS, temperature sensors TS, and semiconductor apparatus SA1 serving as the A/D converter unit ADU on the wiring board WB1, while mounting other electronic components on the wiring board WB2 separated from the wiring board WB1. This means that it is enabled to reduce the size of the wiring board WB1 having the pulse wave sensor PWS to touch the human body LB mounted thereon. Accordingly, it is possible to achieve reduction of the external size of the wiring board WB1 from a size of a "comfortable" level to the human body LB to a size of an "unaware" level. In the present embodiment, particularly, by implementing dual side mounting, i.e., mounting, mainly, the pulse wave sensor PWS and temperature sensors TS on the surface of the wiring board WB1 and mounting, mainly, the semiconductor apparatus SA1 serving as the A/D converter unit ADU on the rear surface of the board WB1, the wiring board WB1 can further be downsized. That is, in the present embodiment, downsizing the wiring board WB1 can be accomplished by synergy obtained by an effect of separating the wiring boards WB1 and WB2 and an effect of mounting electronic components on both the surfaces of the wiring board WB1. For example, given that a configuration is made such that the semiconductor apparatus SA1 serving as the A/D converter unit ADU is also mounted, together with the pulse wave sensor PWS and temperature sensors TS, on the surface of the wiring board WB1, the external size of the wiring board WB1 would become so large that its touch may create discomfort for the human body LB. In contrast hereto, by implementing dual side mounting, i.e., mounting, mainly, the pulse wave sensor PWS and temperature sensors TS on the surface of the wiring board WB1 and mounting, mainly, the semiconductor apparatus SA1 serving as the A/D converter unit ADU on the rear surface of the board WB1, as in the present embodiment, it can be accomplished to downsize the wiring board WB1.

Furthermore, the configuration in which an A/D converter unit is not incorporated in the pulse wave sensor PWS also contributes to downsizing the wiring board WB1. The reason for this is as follows. Incorporating an A/D converter unit in the pulse wave sensor PWS makes an increase in the size of the pulse wave sensor PWS itself and an A/D converter unit has to be incorporated in a temperature sensor TS as well, mounted, together with the pulse wave sensor PWS, on the surface of the wiring board WB1, which results in increasing the size of a temperature sensor TS as well. That is, if an A/D converter unit is incorporated in the pulse wave sensor PWS, output from the pulse wave sensor PWS becomes a digital signal, whereas output from a temperature sensor TS remains as an analog signal; hence, the temperature sensor TS has to be made to output a digital signal by incorporating an A/D converter unit in it as well. In this case, an A/D converter unit has to be incorporated in the temperature sensor TS as well, not only in the pulse wave sensor PWS. As a result, forming dual AD converter units also causes an increase in the size of the wiring board WB1. In contrast hereto, in the present embodiment, the pulse wave sensor PWS and the A/D converter unit ADU are separate and, therefore, this separate A/D converter unit ADU can be used commonly for the pulse wave sensor PWS and the temperature sensor TS. That is, by the separate A/D converter unit ADU, both A/D conversion of an analog signal from the pulse wave sensor PWS and A/D conversion of an analog signal from the temperature sensor TS can be performed. Consequently, according to the present embodiment, it is only required to provide one A/D converter unit for common use for the pulse wave sensor PWS and the temperature sensor TS; so that, there is no need to provide dual A/D converter units. From this perspective also, it can be accomplished to downsize the wiring board WB1.

Moreover, the configuration in which the pulse wave sensor PWS and the A/D converter unit ADU are separate not only contributes to downsizing the wiring board WB1, as described above, also contributes to improvement in the performance of the sensor node that is robust to noise and capable of detecting a pulse wave with a high accuracy. This point is described below.

For example, in a case where the A/D converter unit ADU is incorporated in the pulse wave sensor PWS, it is difficult to improve the performance of the incorporated A/D converter unit ADU, as compared with an A/D converter unit ADU used as a separated component. The reason for this is as follows. In the case where the A/D converter unit ADU is incorporated in the pulse wave sensor PWS, a requirement to enhance the performance of the A/D converter unit ADU inevitably causes an increase in the size of the pulse wave sensor PWS and a compromise has to be made on the performance of A/D converter unit ADU in order to downsize the pulse wave sensor PWS. In contrast hereto, in an instance where the A/D converter unit ADU is configured as another component separate from the pulse wave sensor PWS, as in the present embodiment, it would become possible to select a dedicated semiconductor apparatus SA1 serving as the A/D converter unit ADU having high performance without regard to downsizing the pulse wave sensor PWS. Thereby, according to the present embodiment, downsizing the pulse wave sensor PWS is compatible with improving the performance in the sensor node ND by adopting an A/D converter unit ADU having high performance.

Furthermore, in the present embodiment, from the perspective of downsizing the wiring board WB1, the pulse wave sensor PWS is mounted on the surface of the wiring board WB1, whereas the semiconductor apparatus SA1 serving as the A/D converter unit ADU is mounted on the rear surface of the wiring board WB1. In this context, particularly, placing the pulse wave sensor PWS and the semiconductor apparatus SA1 serving as the A/D converter unit ADU so that they will overlap planarly also contributes to improvement in the performance of the sensor node. The reason for this is as follows. In an instance where the pulse wave sensor PWS and the semiconductor apparatus SA1 serving as the A/D converter unit ADU are placed to overlap planarly, the pulse wave sensor PWS and the semiconductor apparatus SA1 serving as the A/D converter unit ADU can electrically be coupled with a minimum distance between them by penetrating electrodes (via plugs) which penetrate the wring board. That is, the fact that the pulse wave sensor PWS and the semiconductor apparatus SA1 can be coupled with a minimum distance between them means that the distance of transmission of an analog signal which has been output from the pulse wave sensor PWS can be made shorter. More specifically, because noise is liable to be superimposed on an analog signal, the longer the distance of analog signal transmission, the larger will be the probability that noise enters an analog signal, which results in deteriorating the analog signal. In other words, shortening the distance of analog signal transmission can lead to decreasing the probability that noise enters an analog signal. Therefore, taking account of this fact and that a digital signal to which an analog signal is converted is robust to nose, according to the present embodiment, it is possible to detect a pulse wave with a high accuracy without deteriorating the S/N ratio of a detection signal from the pulse wave sensor PWS. This means that it can be accomplished to improve the performance of the sensor node. In a broader perspective, it is possible to enhance the accuracy of health management with a smartphone through the use of highly accurate biological information (pulse wave)

In turn, a second feature of the present embodiment resides in that the booster unit HVU is mounted on the wiring board WB2, but not on the wiring board WB1. The booster unit HVU has a function of generating a high voltage higher than an operating voltage from the operating voltage that is supplied from the li, lithium ion battery LIB and supplies this high voltage to the pulse wave sensor PWS. Therefore, it can be considered as natural to mount the booster unit HVU on the wiring board WB1 on which the pulse wave sensor PWS is also mounted. However, if a configuration is made such that the booster unit HVU is mounted on wiring board WB1, it is a concern that the HVU causes an adverse effect on the human body LB. That is, the booster unit HVU is configured of, e.g., a DC/DC converter and the DC/DC converter is liable to generate heat. For this reason, if the booster unit HVU is mounted on the wiring board WB1 that is placed nearer to the human body LB, the booster unit HVU naturally becomes closer to the human body LB and this increase a risk of causing a low temperature burn on the human body LB. Moreover, the temperature sensor TS to detect bodily temperature is also mounted on the wiring board WB1. If the booster unit HVU that is liable to generate heat is mounted on the wiring board WB1, there is a fear that the accuracy of the temperature sensor TS in detecting bodily temperature deteriorates under the influence of heat generation from the booster unit HVU. For this reason, in the present embodiment, the semiconductor apparatus SA4 serving as the booster unit HVU that generates heat is mounted on the wiring board WB2 placed far away from the human body LB, but not on the wiring board WB1 placed nearer to the human body LB. According to the present invention, it is thus possible to suppress the risk of causing a low temperature burn on the human body LB and suppress deterioration in the accuracy of the temperature sensor TS in detecting bodily temperature.

Moreover, in the present embodiment, as depicted in FIG. 10, the semiconductor apparatus SA4 serving as the booster unit HVU is mounted on the surface of the wiring board WB2 and this can provide an advantage as noted below. For example, the lithium ion battery LIB is placed on the rear surface of the wiring board WB2 and it is required to maintain the temperature of the lithium ion battery LIB at approx. 60° C., taking safety in account. Hence, for instance, if the semiconductor apparatus SA4 serving as the booster unit HVU is mounted on the rear surface of the wiring board WB2, this semiconductor apparatus SA4 and the lithium ion battery LIB become close to each other. In this case, the lithium ion battery LIB becomes prone to be affected by heat generation from the semiconductor apparatus SA4 and there is a possibility that the temperature of the lithium ion battery LIB may exceed approx. 60° C. For this reason, in the present embodiment, the semiconductor apparatus SA4 serving as the booster unit HVU is mounted on the surface of the wiring board WB2, as depicted in FIG. 10. Thereby, heat generated in the semiconductor apparatus SA4 becomes hard to convey to the lithium ion battery LIB placed on the rear surface of the wiring board WB2 and, consequently, an adverse influence on the lithium ion battery LIB can be suppressed. According to the present embodiment, it is thus possible to suppress a temperature increase of the lithium ion battery LIB because of heat generation by the booster unit HVU, ensure the safety of the lithium ion battery LIB, and eventually improve the reliability of the sensor node ND.

Furthermore, in the present embodiment, the semiconductor apparatus SA4 serving as the booster unit HVU is placed near to the connector CNT, as depicted in FIG. 10. This can increase efficiency of heat dissipation from the semiconductor apparatus SA4 which is a heat generating component. The reason for this is that the connector CNT is configured of metal members having high thermal conductivity and, by placing the semiconductor apparatus SA4 near to the connector CNT, heat generated in the semiconductor apparatus SA4 can efficiently be dissipated from the connector CNT placed beside the semiconductor apparatus SA4. According to the present embodiment, it is thus possible to suppress a temperature increase of the semiconductor apparatus itself SA4 serving as the booster unit HVU and, thereby, it is possible to prevent malfunction of the semiconductor apparatus itself SA4.

Moreover, to prevent malfunction due to heat, it is also effective to place the semiconductor apparatus SA2 serving as the data processing unit DPU and the semiconductor apparatus SA3 serving as the wireless communication unit RFU far away from the semiconductor apparatus SA4 which is a heat generating component, for example, as depicted in FIG. 10. In this case, the semiconductor apparatus SA2 serving as the data processing unit DPU and the semiconductor apparatus SA3 serving as the wireless communication unit RFU become insusceptible to heat from the semiconductor apparatus SA4 mounted on the same wiring board WB2 on which they are also mounted. It is thus possible to suppress malfunction of the semiconductor apparatus SA2 and the semiconductor apparatus SA3 due to heat. Also from this perspective, it is therefore possible to improve the reliability of the sensor node ND.

Then, a third feature of the present embodiment resides in artifices to improve transmitting and receiving characteristics of the antenna ANT1. Specifically, as a first artifice to improve the transmitting and receiving characteristics of the antenna ANT1, the antenna ANT1 mounted on the wiring board WB2 and the connector CNT mounted on the wiring board WB2 are placed farthest from each other, for example, as depicted in FIG. 10. In other words, it can be stated that the antenna ANT1 and the connector CNT are placed in the edges opposite to each other of the wiring board WB2. That is, it can be stated that the antenna ANT1 and the connector CNT are placed in opposite end regions of the wiring board WB2. Thereby, according to the present embodiment, it is possible to improve the transmitting and receiving characteristics of the antenna ANT1. The reason for this is that, because the connector CNT is configured of conductive members, the connector CNT, if placed near to the antenna ANT1, causes an adverse effect on the transmitting and receiving characteristics of the antenna ANT1. That is, the transmitting and receiving characteristics of the antenna ANT1 deteriorate, if conductive members exist near the antenna ANT. Therefore, in the present embodiment, by separating the connector CNT that is configured of conductive members as far as possible from the antenna ANT1, it is possible to minimize an adverse effect caused by the connector CNT on the transmitting and receiving characteristics of the antenna ANT1.

Furthermore, the present invention also includes a second artifice to improve the communication characteristics of the antenna ANT1. The sensor node ND according to the present embodiment is configured such that there is no conductive member that planarly overlaps with the antenna ANT1, for example, as depicted in FIGS. 10 and 12. Specifically, as depicted in FIG. 10, the electronic components and the antenna ANT1 mounted on the wiring board WB2 are placed not to overlap planarly and, besides, the antenna ANT1 is placed not to planarly overlap with the lithium ion battery LIB. Thereby, according to the present embodiment, because there is no conductive member that planarly overlaps with the antenna ANT1, it is possible to improve the transmitting and receiving characteristics of the antenna ANT1 in comparison with a case where there is a conductive member in a region that planarly overlaps with the antenna ANT1.

As will be appreciated from the foregoing, according to the present embodiment, component layout of the sensor node ND is configured, taking the first artifice in which the antenna ANT1 and the connector CNT are placed in opposite end regions and the second artifice in which the sensor node ND does not include a conductive member that planarly overlaps with the antenna ANT1 as a design concept. In consequence, according to the present embodiment, it is possible to accomplish improving the transmitting and receiving characteristics of the antenna ANT1 by a synergetic effect of the first and second artifices.

As noted above, according to the present embodiment, because of its first, second and third features, it is possible to obtain noticeable effects as follows: downsizing the sensor node ND incorporating a biosensor to detect biological information; improving the accuracy of detection made by the biosensor; and realizability of the sensor node ND having good communication characteristics.

<Example of Modification>

Then, an example of modification to the embodiment is described. In the embodiment, a practical application in which the sensor node ND is attached onto the eyeglass frame FR was described, for example, as depicted in FIG. 9. However, a technical concept of the embodiment is not limited to this application and is also applicable to a practical application in which the sensor node ND is attached onto a watch band.

Figure 13A:
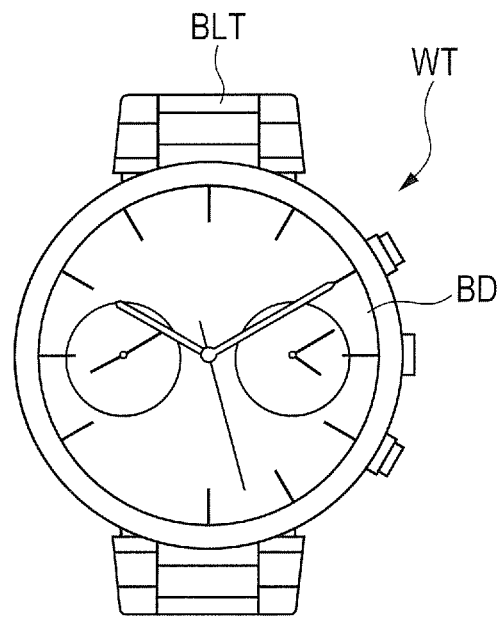
FIG. 13A is a schematic view of a watch viewed from its surface side and FIG. 13B is a schematic view of the watch viewed from its rear surface side.
Figure 13B:
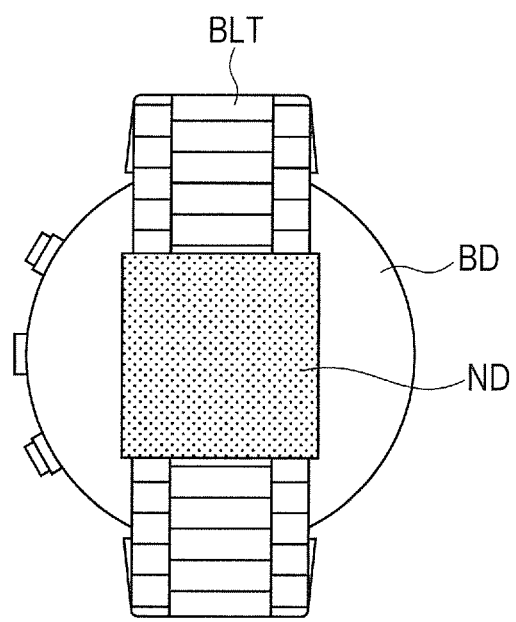

FIGS. 13A and 13B are diagrams depicting a practical application in which the sensor node ND is attached onto a watch WT. In particular, FIG. 13A is a schematic view of the watch WT viewed from its surface side and FIG. 13B is a schematic view of the watch WT viewed from its rear surface side. As depicted in FIG. 13A, the watch WT includes a main body BD including a dial plate and a watch band BLT coupled to the main body BD. Then, the sensor node ND is installed onto the watch band BLT, as depicted in FIG. 13B. Thereby, for instance, when a person wears the watch WT on his or her wrist, the sensor node ND can be set to touch a vascular channel located in the underside of the wrist. Thereby, also in an instance where the sensor node ND is installed onto the watch WT, a pulse wave of a human body can be detected by the pulse wave sensor incorporated in the sensor node ND. Particularly, the practical application in which the sensor node ND is installed onto an eyeglass frame is principally applied to people who wear glasses, whereas the practical application, like this example of modification, in which the sensor node ND is installed onto a watch can be applied to a wider range of people, regardless of whether or not they wear glasses.

While the invention made by the present inventors has been described specifically based on its embodiment hereinbefore, it will be appreciated that the present invention is not limited to the described embodiment and various modifications may be made thereto without departing from the gist of the invention.

What is claimed is:

1. An electronic apparatus comprising:
   a first wiring board that has a first front surface and a first rear surface opposite the first front surface;
   a second wiring board which differs from the first wiring board;
   a biosensor that is mounted on the first front surface of the first wiring board and is to detect biological information;
   an A/D converter unit that is mounted on the first rear surface of the first wiring board and converts an analog signal corresponding to the biological information detected by the biosensor to a digital signal;
   a signal processing unit that is mounted on the second wiring board and takes input of the digital signal which has been output from the A/D converter unit and processes that signal;
   a wireless communication unit that is mounted on the second wiring board and is electrically coupled to the signal processing unit; and
   an antenna that is mounted on the second wiring board and is electrically coupled to the wireless communication unit,
   wherein the biosensor is a pulse wave sensor,
   wherein a temperature sensor is mounted on the first front surface of the first wiring board and detects bodily temperature of a living body, and
   wherein the height of the pulse wave sensor from the first front surface is higher than the height of the temperature sensor from the first front surface to allow the pulse wave sensor to be in contact with the living body,
   wherein the electronic apparatus is configured to be attached to an eyeglass frame,
   wherein the eyeglass frame is disposed between the first rear surface of the first wiring board and the second wiring board,
   wherein a rechargeable battery is disposed between the eyeglass frame and the second wiring board,
   wherein the second wiring board includes a second front surface and a second rear surface opposite the second front surface,
   wherein the second front surface includes a first area and a second area,
   wherein the antenna is mounted in the first area, and
   wherein the rechargeable battery is disposed so as not to overlap with the first area of the second front surface.

2. The electronic apparatus according to claim 1,
   wherein the biosensor is placed to be allowed to touch the living body.

3. The electronic apparatus according to claim 1,
   wherein the first rear surface of the first wiring board faces the second wiring board.

4. The electronic apparatus according to claim 3,
   wherein the second rear surface of the second wiring board faces the first rear surface of the first wiring board, and
   wherein the second wiring board further comprises a connector that is mounted on the second front surface and electrically coupled to the rechargeable battery and through which a charging current passes through when the rechargeable battery is charged.

5. The electronic apparatus according to claim 4,
   wherein the antenna and the connector are placed at opposite ends of the second wiring board.

6. The electronic apparatus according to claim 3,
   wherein the second rear surface of the second wiring board faces the first rear surface of the first wiring board, and
   wherein the second wiring board further comprises a booster unit that is mounted on the second front surface and, from a supply voltage that is supplied from the rechargeable battery, generates a first voltage higher than the supply voltage.

7. The electronic apparatus according to claim 6,
   wherein the booster unit supplies the first voltage to the biosensor.

8. The electronic apparatus according to claim 1, wherein the external size of the first wiring board is smaller than the external size of the second wiring board.

9. The electronic apparatus according to claim 1, wherein the electronic apparatus does not comprise a conductive member that overlaps with the antenna.

* * * * *